United States Patent [19]

Neier et al.

[11] Patent Number: 4,546,206

[45] Date of Patent: Oct. 8, 1985

[54] PROCESS FOR PRODUCING METHYL TERT. ALKYL ETHER

[75] Inventors: Wilhelm Neier; Werner Webers, both of Rheinberg; Michael Dettmer, Glinde, all of Fed. Rep. of Germany

[73] Assignee: Deutsche Texaco Aktiengesellschaft, Hamburg, Fed. Rep. of Germany

[21] Appl. No.: 620,657

[22] Filed: Jun. 14, 1984

[30] Foreign Application Priority Data

Jun. 24, 1983 [DE] Fed. Rep. of Germany ....... 3322753

[51] Int. Cl.$^4$ ..................... C07C 41/06; C07C 43/04
[52] U.S. Cl. .................................... 568/697
[58] Field of Search .......................... 568/697

[56] References Cited

U.S. PATENT DOCUMENTS 4,262,146 4/1981 Childs ................................ 568/697
4,320,233 3/1982 Makovec et al. .................. 568/697

Primary Examiner—J. E. Evans
Attorney, Agent, or Firm—Robert A. Kulason; James J. O'Loughlin; Carl G. Seutter

[57] ABSTRACT

Methyl t-butyl ether and methyl t-amyl ether are produced by reacting methanol with isobutene and isoamylene, respectively, at a total methanol/isoolefine mole ratio of 1–1.2:1 in a series of reaction stages such that in the first reaction stage, the total amount of olefin component is reacted with as much methanol as is required to ensure that the methanol/isoolefine mole ratio in the first reaction stage does not drop to less than 0.65:1, and that the methanol concentration in the effluent stream does not exceed 0.4% wt. The residual amount of methanol is then fed either all at once to another reaction stage, or in portions to several additional reaction stages.

18 Claims, 1 Drawing Figure

PROCESS FOR PRODUCING METHYL TERT. ALKYL ETHER

The invention relates to a process for producing methyl tert.-butyl ether and methyl tert.-amyl ether by reacting isobutene, particularly an isobutene-containing $C_4$-hydrocarbon cut, and isoamylene, respectively, particularly an isoamylene-containing $C_5$-hydrocarbon cut, with methanol at a methanol/isoolefine mole ratio of 1–1.2:1 in the presence of acidic solid catalysts in several reaction stages.

BACKGROUND OF THE INVENTION

It is known that, in the synthesis of methyl tert.butyl ether (MTBE), dimethyl ether (DME) is formed as a by-product, depending on the reaction conditions. This dimethyl ether remains in the product raffinate after washing with water and distillation (if the reaction mixture is washed with water). For the further processing, different requirements are made on this raffinate. In some cases higher DME contents may be tolerated. In other processes (e.g. the HF-alkylation) too high a DME content may cause noticeable trouble. Therefore, if the raffinate is intended for further processing, as in HF-alkylation, a product purity of max. 10 to 15 ppm of DME in the raffinate is required.

In the prior art processes, the DME content in the raffinate may be as high as 100–300 ppm. To remove the DME from the raffinate, repeated stripping of the raffinate is necessary (see Chemistry and Industry, Aug. 21, 1982, page 570 ff). Since this raffinate, if starting from a $C_4$-hydrocarbon cut from a steam cracker or an FCC unit, often contains besides the $C_4$-components also noticeable amounts of propane and propylene (3 to 10%), the separation of DME is elaborate and expensive because DME forms with propane an azeotrope containing 8% DME.

In the synthesis of methyl tert.-amyl ether (TAME), dimethyl ether (DME) is formed as a by-product as well.

In general, alcohol to isoolefine mole ratios of 0.5–6:1, preferably 1–2:1, are recommended for the etherification of isobutene and isoamylene, respectively, with methanol. According to the prior art, the reaction temperature may be 50° C.–120° C., preferably 70° C.–120° C., and the appropriate reaction pressure is 5–50 bar; see for instance DE-OS 29 11 077, pages 4 and 5, and European Patent Application 0015 513, page 6. It is also known that the first reaction stages may be provided with circuits for removing the reaction heat, see SRI-Report 76-1-1, page 5/6.

In U.S. Pat. No. 4,262,146 it is suggested to split up the hydrocarbon stream in order to control the temperature; depending on the temperature rise in the first reactor, part of the isoolefine component by-passes the first reactor and is introduced into the second reactor.

In none of the known publications is the formation of DME considered. Attention is rather paid to procedures for separating DME from the product stream.

It is an object of this invention to perform the MTBE synthesis and the TAME synthesis such that the DME formation is suppressed to the extent that subsequent removal of DME from the raffinate can be omitted. Other objects will be apparent to those skilled in the art.

STATEMENT OF THE INVENTION

In accordance with certain of its aspects, this invention is directed to a process for producing methyl t-alkyl ether selected from the group consisting of methyl t-butyl ether and methyl t-amyl ether by the reaction of isobutene and isoamylene, respectively, with methanol in the presence of acidic solid catalyst in several reaction stages which comprises passing to the first reaction stage the total amount of isoolefine charge and a first portion of the methanol charge; controlling the rate of feed of the first portion of methanol to the first reaction stage whereby the concentration of methanol in the effluent therefrom does not exceed 0.4 w % and the mole ratio in said first reaction stage does not fall below 0.65:1; adding the residual portion of methanol to the effluent from the first reaction stage in at least one additional reaction stage; and maintaining the total mole ratio of methanol to isoolefine at 1–1.2:1.

DESCRIPTION OF THE INVENTION

The charge hydrocarbon stream which may be employed in practice of the process of this invention is an isoolefine-containing stream. Although it is possible to operate using a substantially pure isoolefine stream, in preferred practice of the process, the charge hydrocarbon may be a $C_4$ hydrocarbon stream and a $C_5$ hydrocarbon stream, respectively. A typical $C_4$ stream derived from a TCC off-gas may contain 13.2 w % isobutene together with insert hydrocarbons (i.e. hydrocarbons which do not react in the instant process).

The charge methanol may be the anhydrous methanol of commerce.

In practice of the process of this invention, the reaction may be carried out in a series of reaction zones. There may preferably be 2–3 reaction zones; and although they may be within separate shells, it is preferred that they be within one shell. Each reaction zone may contain therein a bed of solid resin etherification catalyst, typefied by those available under the trademarks Lewatite SPC 118, Duolite C26 or preferably Amberlyst 15. The latter is the trademark for a solid, acidic, resin etherification catalyst containing sulfonated polystyrene which has been cross-linked with divinylbenzene.

The overall mole ratio of methanol to isoolefine is maintained at 1–1.2:1.

All the isoolefine charge is admitted to the first reaction stage together with a first portion of the methanol charge. There may also be preferably admitted to the first reaction stage, a recycled portion of the effluent therefrom.

The stream entering the first reaction stage is controlled to maintain, at the admission thereto, a mole ratio of methanol to isobutene of 0.65–0.9:1. This may be done by controlling the amount of recycle or the amount of fresh charge methanol admitted thereto.

Reaction in the first reaction stage proceeds at typically 40° C.–80° C., say 60° C. in liquid phase in the presence of the catalyst to yield product stream containing methyl tertiary-butyl ether and methyl tertiary-amyl ether, respectively.

It is a feature of the process of this invention that operation in the first reaction stage is controlled so that the concentration of methanol in the effluent therefrom does not exceed 0.4 w % and the mole ratio of methanol to isoolefine in the first reaction stage does not fall below 0.65:1. This control may be effected by adjusting the amount of methanol admitted to the first reaction stage.

Effluent from the first reaction stage is withdrawn therefrom. A portion thereof is returned as recycle to the charge to the first reaction stage. A heat exchanger is preferably included in the recycle circuit to remove the heat of reaction from the recycle and to maintain the first reaction stage at desired temperature.

The remaining portion of the effluent from the first reaction stage is passed to the second reaction stage. Also admitted to this second stage are (i) a second porton of the isobutene charge and (ii) a portion of the effluent from the second reaction stage. The temperature of this total charge is adjusted to remove the heat generated by the reaction and the total is admitted to the second reaction stage. Etherification occurs herein in manner comparable to reaction in the first reaction stage.

When the process is carried out using three stages, as in the preferred embodiment, the effluent from the second reaction stage is split, the one portion being recycled to the charge to the second reaction stage and the other portion being passed as charge to the third reaction stage to which is also admitted (i) a further portion, and in the preferred embodiment the remaining portion, of the methanol charge and (ii) as recycle a portion of the effluent from the outlet of the third reaction stage.

The etherification reaction occurs in the third reaction stage in manner comparable to that of the first and second stages; the effluent therefrom is recovered.

It is a feature of the process of this invention, when the total mole ratio of methanol to isobutene is 1-1.2:1 and the other conditions noted herein are followed, that the content of DME in the product stream is decreased to as low as 5 ppm.

Experiments have shown that with the usual excess operation (methanol/isoolefine ratio greater than 1:1) the formation of ether is independent of the mole ratio. Though it is possible to lower the formation of DME from greater than 100 ppm to about 50 ppm by using the lowest possible reaction temperatures, it is known that thereby the conversion drops considerably. The residual isobutene content is then 2.5%.

The problem is solved by the instant process characterized by reacting methanol and isoolefine at a total methanol to isoolefine mole ratio of 0.65-0.9:1 in the first reaction stage and reacting in the first reaction stage the total amount of olefin component with part of the methanol, the methanol feed being controlled so that the methanol concentration of the effluent stream of the first reaction stage does not exceed 0.4 w % and the methanol to isoolefine mole ratio does not drop below 0.65:1 in the first reaction stage, and by charging the remaining methanol to a further reaction stage, or by charging it in portions to several additional reaction stages.

For, it has been surprisingly found that if all of the hydrocarbon cut is charged at once to the first reaction stage and the methanol feed is apportioned to the first and the second reaction stages, (preferably to the first, second, and third reaction stages) the formation of DME can be lowered such that the DME content in the reactor effluent is down to below 5 ppm. The methanol feed is controlled so that the methanol concentration in the effluent of the first reaction stage is max. 0.4%, preferably less than 0.1%. During this mode of operation which has a recycle ratio (i.e. recycled quantities vs. fresh hydrocarbon cut feed plus methanol) of preferably at least about 2, about 0.65-0.9, preferably 0.7-0.85 mole of methanol per mole of isoolefine is fed to the first reaction stage. In the second reaction stage, methanol is charged in amount sufficient to ensure that the methanol concentration in the effluent of this section does not exceed 0.4%, preferably 0.1%. In this mode of operation additional methanol, (0.1-0.3 mole per mole of isoolefine feed) can be charged to the second reaction stage.

The remaining quantity of methanol (up to a methanol to isoolefine mole ratio of 1:1 to 1.2:1, preferably 1.05 to 1.15:1) is fed to the charge stream to the third reaction stage. The instant process can be advantageously conducted at a recycle ratio of 2:1 to 10:1, preferably 3:1 to 5:1, in the first two reaction stages.

Since DME formation is found to be essentially constant as methanol concentration increases from 1.5% to 18% in the reactor effluent, it is surprising with the instant process that by further lowering of the methanol content to 0.4, preferably to 0.1%, a noticeable decrease in DME formation was observed. According to literature data, the lowering of the methanol isoolefine mole ratios of less than 1:1 was not advisable (see e.g. European patent application 0 071 238, page 10), because in this case oligomerization or polymerization takes place, which also affects the catalyst.

According to the process of the instant invention, it was also found that a methanol to isoolefine ratio of 0.6:1 in the first reaction stage, oligomers are formed in the range of 3 to 5%, relative to MTBE and TAME, respectively. The side reaction further further increases as the methanol ratio decreases. It is surprising that this oligomerization can be lowered to the same extent (to below 0.2%). as with a methanol ratio of above 1:1 if the methanol is charged to the recycle stream of the first reaction stages such that a methanol ratio of about 0.65-0.9:1, preferably 0.70 to 0.85, is attained, while simultaneously the methanol concentration is below 0.1%.

DESCRIPTION OF THE DRAWING ON THE BASIS OF THE PROCESS FOR PRODUCING MTBE

The drawing shows a schematic representation of a flow sheet according to which the process of this invention may be carried out.

In the drawing, charge isobutene is admitted through lines 10 and 11 to reactor 12 which include a first reaction stage 13 in which is a bed of catalyst: Amberlyst 15 brand of polystyrene (cross-linked with divinyl benzene) beads.

Methanol is admitted through line 14; and a portion thereof is passed through lines 15 and 16 to join with the charge isobutene passing through lines 10 and 11. The stream in line 11 is cooled in heat exchanger 17 to about 65° C.

Reaction in the catalyst bed in first reaction stage 13 occurs between isobutene and methanol to produce a product stream containing methyl tertiary-butyl ether, recovered through line 18. A portion of this stream is withdrawn and passed as recycle through line 19 and pump 20 and line 16 to line 11.

The remainder of the stream in line 18 is passed through lines 21 and 22 to second reaction stage 23. Also admitted to line 22 through lines 24 and 25 is a second portion of methanol; and a recycle stream is admitted from line 26 and pump 27. Heat exchanger 29 in line 22 cools the charge stream entering stage 23.

Reaction in the catalyst bed in second reaction stage 23 occurs between isobutene and methanol to produce a product stream containing methyl tertiary-butyl ether, recovered through line 28. A portion of this stream is withdrawn and passed as recycle through line 26 and pump 27 to line 22.

The remainder of the stream in line 28 is passed through lines 30 and 31 to third reaction stage 32. Also admitted to line 31 through line 33 is a second portion of methanol; and a recycle stream is admitted from line 34 and pump 35. Heat exchanger 36 in line 31 cools the charge stream entering stage 32.

Reaction in the catalyst bed in third reaction stage 32 occurs between isobutene and methanol to produce a product stream containing methyl tertiary-butyl ether, recovered through line 37. A portion of this stream is withdrawn and passed as recycle through line 34 and pump 35 to line 31.

The remainder of the stream in line 37 is withdrawn as product through line 38.

DESCRIPTION OF PREFERRED EMBODIMENTS

Figure 1:
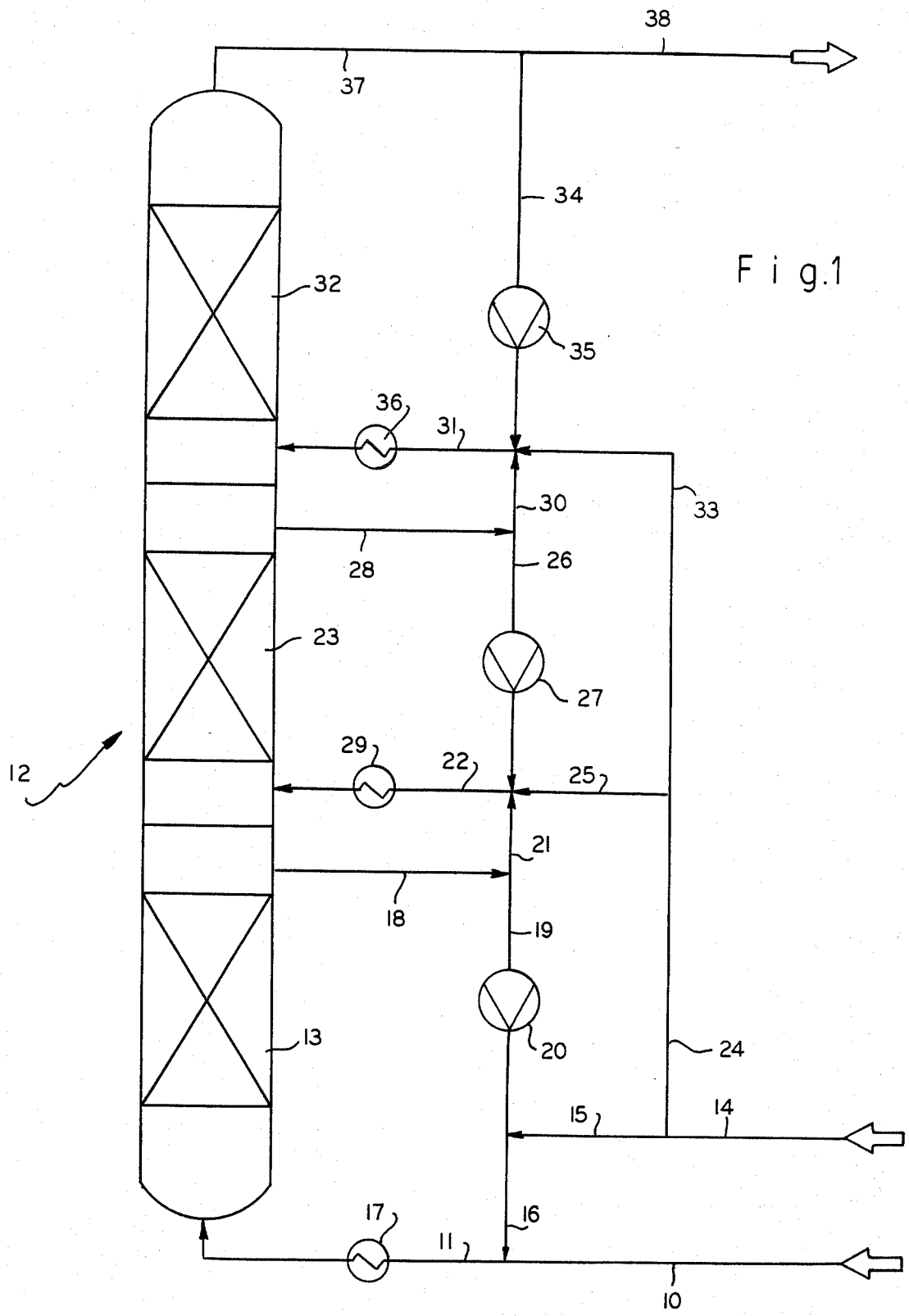

Practice of the process of this invention will be apparent to those skilled in the art from the following examples wherein, as elsewhere in this specification, all parts are parts by weight unless otherwise stated.

The apparatus included three reactor stages having an internal diameter of 26 mm and individual lengths of 3.0 m, 1.5 m, and 3.0 m. The catalyst volumes were 1100 ml, 550 ml, and 925 ml. A dry, strongly acidic, macroporous, commercial cation exchanger (Amberlyst 15) was used as catalyst. (Other catalysts, such as Lewatit SPC 118, Doulite C 26, etc show the same behavior). The reactions were carried out as shown in the process flow sheet of the drawing.

EXAMPLE I*

4,600 grams/h of a 13.2% isobutene-containing TCC gas were charged through line 10 into reactor stage 13, and 390 grams/h of methanol (methanol/isobutene mole ratio 1.12:1) were charged through lines 14, 15, 16, LHSV=3.3/h. In each of the three reactor stages a max. temperature of 65° C. was maintained. Using the pumps 20 and 27 a recycle quantity of 20 liters/h was adjusted in the first two reactor stages. The third reactor stage was operated without recycling of the reaction product in this embodiment. The reaction pressure was 10 bar.

Under these conditions isobutene was converted up to a residual content of 0.7% in the raffinate (95% conversion). The methanol content was 1.9% in the recycle product of the first reactor stage, 1.4% in the recycle product of the second stage, and 1.2% after the third stage. In the reactor effluent a DME content of 190 to 200 ppm was observed.

EXAMPLE II*

The run described in Control Example I* was repeated, the difference being that the methanol feed was raised to 1,440 g/h (methanol to isobutene mole ratio 4.13:1). All the other conditions were maintained the same. Due to the higher methanol feed, the LHSV increased from 3.3 to 3.7/h. The methanol concentration in the individual reactor stages was: 18.9% in the recycle product of the first stage; 18.5% in the recycle product of the second stage; and 18.4% after the third reactor stage. The residual isobutene content in the product was 0.7%, and the DME content was 190 to 230 ppm.

EXAMPLE III*

The run described in Control Example I* was repeated, the differences being as follows: The temperatures were lowered to 50° C. in the first stage and to 45° C. in the following two reaction stages. At the same time, the LHSV was changed to 2.0/h; the methanol to isobutene mole ratio was lowered to 1.12:1, i.e. 2,850 g/h of TCC gas and 242 g/h of methanol were fed. The recycle quantities were maintained constant. Under these conditions an isobutene conversion of 83% (2.5% residual isobutene content) and DME contents of 45 to 50 ppm in the reactor effluent were obtained. The amount of oligomers (mainly diisobutene) was below 0.2% relative to the formed MTBE.

EXAMPLE IV

This Example sets forth the best mode presently known of carrying out the process of this invention. The run described in Control Example III* was repeated, the difference being that methanol was charged both to the first reactor stage and to the second. The methanol concentration in the recycle product of the first stage was below 0.1%, 1.4% in the recycle product of the second stage, and 1.2% in the reactor effluent. 160 g/h of methanol (corresponding to a methanol to isobutene mole ratio of 0.75:1) were charged to the recycle of the first reactor stage, and 82 g/h of methanol were fed to the recycle of the second reactor stage. A conversion of 95% (residual isobutene content=0.8%) and a DME content of 10 to 15 ppm in the reactor effluent was obtained. The formation of oligomers (di- and triisobutylene) was below 0.2%.

EXAMPLE V

The run described in Control Example III* was repeated, the difference being that the methanol feed of 242 grams per hour was distributed as follows among the three reactor stages: 175 g/h were charged to the recycle of the first stage, 25 g/h of methanol were fed to the recycle of the second stage, and 42 g/h were charged into the inlet of the third reactor stage. The methanol contents in the recycle products and in the reactor effluent, respectively, were 0.1% in recycle in line 19, below 0.1% in recycle line 26, and 1.1% after the third reactor stage in line 34. The isobutene conversion was 96% (residual isobutene was 0.7%). The formation of oligomers was below 0.2% and the DME content in the reactor effluent was 2 to 5 ppm.

EXAMPLE VI*

The run described in Control Example I* was repeated, the difference being that the methanol dosage into the recycle of the first reactor stage was lowered from 160 g/h to 125 g/h, corresponding to a methanol to isobutene mole ratio of 0.58:1. The methanol concentration in the reactor effluent was below 0.1%. Additional 117 g of methanol were charged to the recycle of the second stage. The other conditions remained unchanged. The isobutene conversion was 93% (residual isobutene content was 1.0%). The DME content was 10 to 15 ppm, the amount of diisobutene plus oligomers in the MTBE was now 3 to 5%.

EXAMPLE VII*

The run described in Control Example I* was repeated, the difference being that the methanol dosage into the recycle of the first reactor stage was raised to 193 g/h, corresponding to a methanol to isobutene mole ratio of 0.9:1, while the other conditions remained unchanged. The methanol concentration in the reactor effluent was 1.6%. Additional 49 g/h of methanol were charged to the recycle of the second stage. An isobutene conversion of 90% was obtained (residual isobutene content was 1.5%). Under these conditions the DME content increased to 30 to 40 ppm.

EXAMPLE VIII*

In the described apparatus runs were carried out using a C5-cut containing 8.5 w% iso-amylene (2-methyl-butene-1 and 2-methyl-butene-2), 4.250 g/h of C5-cut were charged through line 10 into reactor stage 13, and 205 g/h of methanol (methanol/isoamylene mole ratio 1.24:1) were charged through line 14, 15, 16, LHSV approx. 2.5 g/h. Using the pumps 20 and 27 the recycle stream was maintained, as before, at 20 l/h each. The reaction pressure was 10 bar, the temperature was 60° C. Under these conditions a 90% conversion of isoamylene into tert. amyl methyl ether (TAME) was obtained. In the reactor effluent a DME content of 200 ppm was observed.

EXAMPLE IX

The run described in Control Example VI* was repeated, the difference being that 125 g/h of methanol were charged to reactor stage 13 corresponding to a methanol to isoamylene mole ratio of 0.76:1. In addition, 20 g/h and 60 g/h of methanol were charged to the reactor stages 23 and 32 resp. The temperature in the third stage was lowered to 50° C. Under these conditions a 92% conversion of isoamylene into TAME was obtained. In the reactor effluent a DME content of 15 ppm was observed.

Although this invention has been illustrated by reference to specific embodiments, it will be apparent to those skilled in the art that various changes and modifications may be made which clearly fall within the scope of this invention.

We claim:

1. The process for producing methyl t-alkyl ether selected from the group consisting of methyl t-butyl ether and methyl t-amyl ether by the reaction of isobutene and isoamylene, respectively, with methanol in the presence of acidic solid catalyst in several reaction stages which comprises
   passing to the first reaction stage the total amount of isoolefine charge and a first portion of the methanol charge;
   controlling the rate of feed of the first portion of methanol to the first reaction stage whereby the concentration of methanol in the effluent therefrom does not exceed 0.4 w% and the mole ratio of methanol to isoolefine admitted to said first reaction stage does not fall below 0.65:1;
   adding the residual portion of methanol to the effluent from the first reaction stage in at least an additional reaction stage; and
   maintaining the total mole ratio of methanol to isoolefine at 1–1.2:1.

2. The process for producing methyl t-alkyl ether selected from the group consisting of methyl t-butyl ether and methyl t-amyl ether as claimed 1 wherein the mole ratio of methanol to isoolefine in the charge to the first reaction stage is controlled to yield effluent therefrom containing not more than about 0.1 w% methanol.

3. The process for producing methyl t-alkyl ether selected from the group consisting of methyl t-butyl ether and methyl t-amyl ether as claimed in claim 1 wherein the mole ratio of methanol to isoolefine in the first reaction stage is 0.65–0.9:1.

4. The process for producing methyl t-alkyl ether selected from the group consisting of methyl t-butyl ether and methyl t-amyl ether as claimed in claim 1 wherein the mole ratio of methanol to isoolefine in the first reaction stage is 0.70–0.85:1.

5. The process for producing methyl t-butyl ether as claimed in claim 1 wherein the isobutene charge is present in an isobutene-containing C4 hydrocarbon stream.

6. The process for producing methyl t-amyl ether as claimed in claim 1 wherein the isoamylene charge is present in an isoamylene-containing C5 hydrocarbon stream.

7. The process for producing methyl t-butyl ether by the reaction of isobutene, in a charge C4 hydrocarbon stream, with charge methanol in the presence of acidic solid catalyst in several reaction stages which comprises
   passing to the first reaction stage the total amount of isobutene charge and a portion of the methanol charge;
   controlling the rate of feed of methanol to the first reaction stage whereby the concentration of methanol in the effluent therefrom does not exceed 0.4% and the mole ratio of methanol to isoolefine admitted to said first reaction stage does not fall below 0.65:1;
   adding the residual portion of methanol to the effluent from the first reaction stage in at least one additional reaction stage; and
   maintaining the total mole ratio of methanol to isobutene at 1–1.2:1;
   thereby producing product stream containing product methyl t-butyl ether and unreacted isobutene; and
   recycling a recycle portion of said product stream to said first reaction stage.

8. The process for producing methyl t-butyl ether as claimed in claim 7 wherein the ratio of (i) said recycle portion of said product stream to (ii) said charge hydrocarbon stream plus charge methanol is greater than about 2.

9. The process for producing methyl t-butyl ether as claimed in claim 7 wherein said reaction is carried out in at least two reaction stages in addition to the first reaction stage and there is admitted to the second reaction stage a second portion of methanol the amount of which is controlled to yield a methanol content in the effluent from the second stage of less than about 0.4 w%.

10. The process for producing methyl t-butyl ether as claimed in claim 7 wherein said reaction is carried out in at least two reaction stages in addition to the first reaction stage and there is admitted to the second reaction stage a second portion of methanol the amount of which is controlled to yield a methanol content in the effluent from the second stage of less than about 0.1 w%.

11. The process for producing methyl t-butyl ether as claimed in claim 7 wherein a portion of the product stream from each reaction stage is recycled to said reaction stage and the charge methanol is admitted to each reaction stage with the recycle to that stage.

12. The process for producing methyl t-butyl ether as claimed in claim 7 wherein said reaction is carried out at 35° C.–70° C. and 5–50 bar.

13. The process for producing methyl t-amyl ether by the reaction of isoamylene, in a charge $C_5$ hydrocarbon stream, with charge methanol in the presence of acidic solid catalyst in several reaction stages which comprises passing to the first reaction stage the total amount of isoamylene charge and a portion of the methanol charge;

controlling the rate of feed of methanol to the first reaction stage whereby the concentration of methanol in the effluent therefrom does not exceed 0.4% and the mole ratio of methanol to isoolefine admitted to said first reaction stage does not fall below 0.65:1;

adding the residual portion of methanol to the effluent from the first reaction stage in at least one additional reaction stage; and maintaining the total mole ratio of methanol to isoamylene at 1–1.2:1;

thereby producing product stream containing product methyl t-amyl ether and unreacted isoamylene; and recycling a recycle portion of said product stream to said first reaction stage.

14. The process for producing methyl t-amyl ether as claimed in claim 13 wherein the ratio of (i) said recycle portion of said product stream to (ii) said charge hydrocarbon stream plus charge methanol is greater than about 2.

15. The process for producing methyl t-amyl ether as claimed in claim 13 wherein said reaction is carried out in at least two reaction stages in addition to the first reaction stage and there is admitted to the second reaction stage a second portion of methanol the amount of which is controlled to yield a methanol content in the effluent from the second stage of less than about 0.4 w%.

16. The process for producing methyl t-amyl ether as claimed in claim 13 wherein said reaction is carried out in at least two reaction stages in addition to the first reaction stage and there is admitted to the second reaction stage a second portion of methanol the amount of which is controlled to yield a methanol content in the effluent from the second stage of less than about 0.1 w%.

17. The process for producing methyl t-amyl ether as claimed in claim 13 wherein a portion of the product stream from each reaction stage is recycled to said reaction stage and the charge methanol is admitted to each reaction stage with the recycle to that stage.

18. The process for producing methyl t-amyl ether as claimed in claim 13 wherein said reaction is carried out at 35° C.–70° C. and 5–50 bar.

* * * * *